United States Patent
Paul et al.

(10) Patent No.: US 9,198,726 B2
(45) Date of Patent: Dec. 1, 2015

(54) PHOTODYNAMIC-BASED CARDIAC ABLATION DEVICE AND METHOD VIA THE ESOPHAGUS

(75) Inventors: Saurav Paul, Minnetonka, MN (US); Israel A. Byrd, Richfield, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 1491 days.

(21) Appl. No.: 11/967,350

(22) Filed: Dec. 31, 2007

(65) Prior Publication Data
US 2009/0171337 A1    Jul. 2, 2009

(51) Int. Cl.
| A61B 18/18 | (2006.01) |
| A61B 18/24 | (2006.01) |
| A61N 5/06  | (2006.01) |
| A61B 18/22 | (2006.01) |

(52) U.S. Cl.
CPC .............. *A61B 18/24* (2013.01); *A61N 5/0601* (2013.01); *A61N 5/062* (2013.01); *A61B 2018/2272* (2013.01)

(58) Field of Classification Search
CPC ........ A61B 18/18; A61B 18/20; A61B 18/22; A61B 18/24; A61B 2018/2272; A61B 2018/2277; A61B 2018/2283; A61B 2018/00053; A61B 2018/00636; A61B 2018/00642; A61N 5/06; A61N 5/0601; A61N 5/062
USPC ................ 606/2–19; 128/898; 607/88, 89, 92
See application file for complete search history.

(56) References Cited

U.S. PATENT DOCUMENTS

| 5,026,366 | A | * | 6/1991 | Leckrone ............................. 606/7 |
| 5,242,437 | A | * | 9/1993 | Everett et al. .................... 606/15 |
| 5,242,438 | A | * | 9/1993 | Saadatmanesh et al. ....... 606/15 |
| 5,275,597 | A |   | 1/1994 | Higgins et al. |
| 5,370,640 | A | * | 12/1994 | Kolff .................................. 606/2 |
| 5,445,608 | A | * | 8/1995 | Chen et al. ....................... 604/20 |
| 5,454,807 | A | * | 10/1995 | Lennox et al. ................... 606/15 |
| 5,865,801 | A |   | 2/1999 | Houser |
| 6,071,276 | A | * | 6/2000 | Abela .............................. 606/27 |
| 6,076,948 | A |   | 6/2000 | Bukosky et al. |
| 6,143,019 | A | * | 11/2000 | Motamedi et al. .............. 607/89 |
| 6,579,285 | B2 |  | 6/2003 | Sinofsky |
| 6,749,623 | B1 | * | 6/2004 | Hsi et al. .......................... 607/88 |
| 6,811,562 | B1 |   | 11/2004 | Pless |
| 7,107,996 | B2 | * | 9/2006 | Ganz et al. ..................... 128/898 |

(Continued)

OTHER PUBLICATIONS

International Search Report and Written Opinion for PCT/US2008/086565 mailed Jan. 29, 2009.

(Continued)

*Primary Examiner* — Ahmed Farah
(74) *Attorney, Agent, or Firm* — Dykema Gossett PLLC

(57) ABSTRACT

A method and system for ablation of cardiac tissue in a living being via the esophagus is provided. The method includes the step of introducing a photodynamic substance to the cardiac tissue. A deformable, elongated body defining a proximal end and a distal end is inserted into an esophagus of the living being. The distal end of the elongated body is located proximate the cardiac tissue. A first set of electromagnetic radiation is then directed from the distal end of the elongated body towards the cardiac tissue. Reflective and opaque surfaces at the distal end of the elongated body may be used to direct the electromagnetic radiation and an expandable membrane at the distal end may be used to urge the distal end of the elongated body to a predetermined position within the esophagus.

9 Claims, 3 Drawing Sheets

(56) References Cited

U.S. PATENT DOCUMENTS

| | | | |
|---|---|---|---|
| 7,996,078 B2* | 8/2011 | Paul et al. | 604/21 |
| 2002/0128636 A1* | 9/2002 | Chin et al. | 606/16 |
| 2008/0077126 A1* | 3/2008 | Rashidi | 606/34 |
| 2008/0115793 A1* | 5/2008 | Roschak | 128/898 |
| 2009/0299354 A1* | 12/2009 | Melsky et al. | 606/16 |
| 2011/0276046 A1* | 11/2011 | Heimbecher et al. | 606/35 |
| 2012/0035603 A1* | 2/2012 | Lenihan | 606/27 |

OTHER PUBLICATIONS

Overholt et al., Photodynamic Therapy for Barrett's Esophagus: Cardiac Effects, Lasers in Surgery and Medicine 21:317-320 (1997).

* cited by examiner

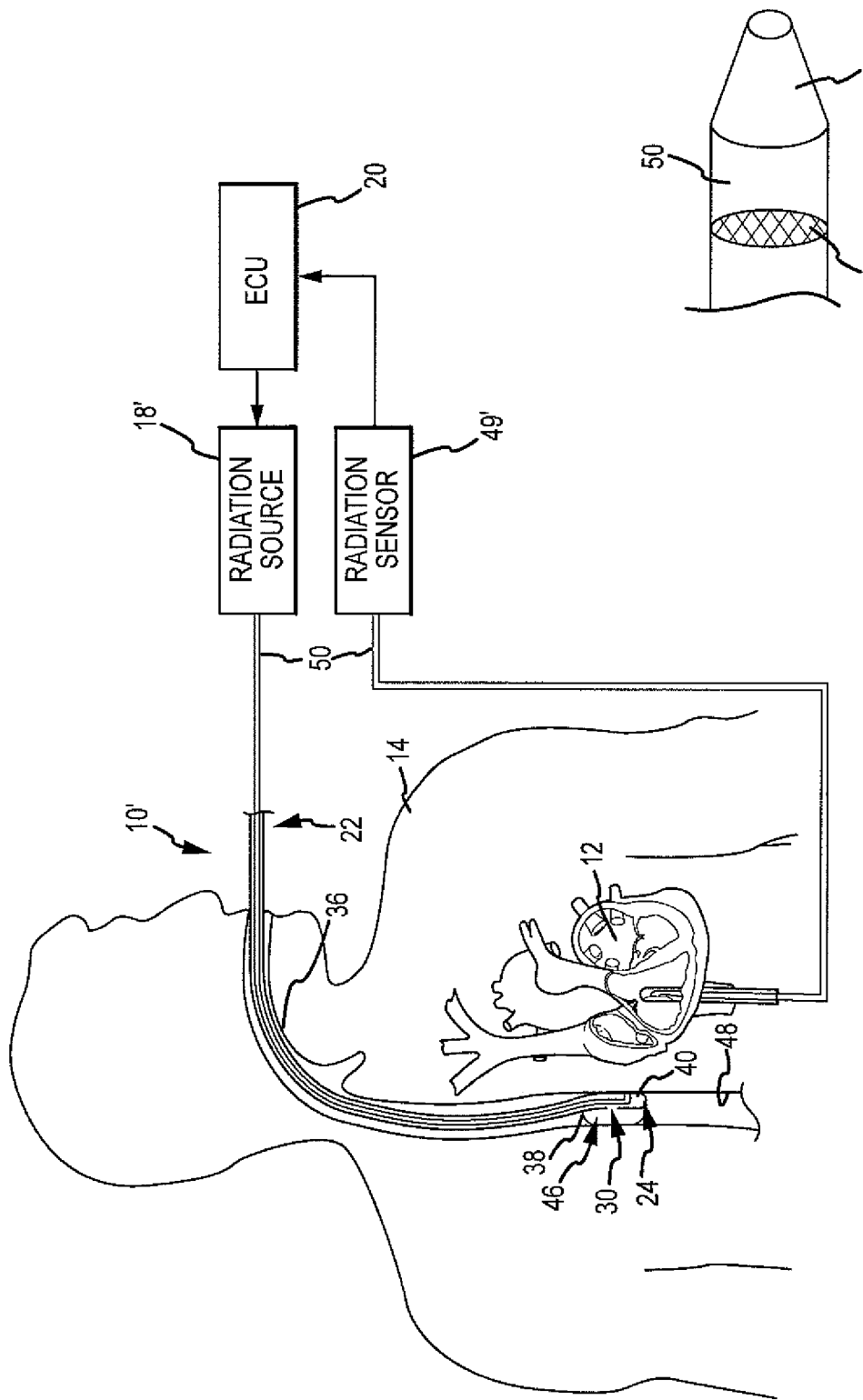

PHOTODYNAMIC-BASED CARDIAC ABLATION DEVICE AND METHOD VIA THE ESOPHAGUS

BACKGROUND OF THE INVENTION a. Field of the Invention

This invention relates to a system and method for ablation of cardiac tissue in a living being. In particular, the instant invention relates to a system and method for ablation of cardiac tissue via the esophagus using photodynamic therapy.

b. Background Art

It is well known to use ablation catheters to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radio frequency energy) to the heart tissue to create a lesion in the heart tissue. This lesion disrupts undesirable electrical pathways and thereby limits or prevents stray electrical signals that lead to arrhythmias.

Ablation catheters are typically placed near the cardiac tissue to be treated in one of two ways. Access to endocardial tissue is obtained by inserting the catheter within a vessel located near the surface of a patient's body (e.g., in an artery or vein in the leg, neck, or arm) and maneuvering the catheter through the circulatory system to the internal heart chambers. Access to epicardial tissue may be obtained by making a subxiphoid incision in the patient's body. Although the use of ablation catheters in this manner has resulted in less invasive treatment of arrhythmias, it would be desirable to develop a system and method for treatment of cardiac tissue that is even less invasive than current methods.

The inventors herein have recognized a need for a system and method for ablation of cardiac tissue that will minimize and/or eliminate one or more of the above-identified deficiencies.

BRIEF SUMMARY OF THE INVENTION

It is desirable to provide a minimally invasive system and method for ablation of cardiac tissue in a living being. In particular, it is desirable to be able to ablate cardiac tissue without requiring surgical incisions or extensive maneuvering within the patient's circulatory system.

A method for ablation of cardiac tissue in a living being in accordance with the present teachings includes the step of introducing a photodynamic substance to the cardiac tissue. The method further includes the steps of inserting a deformable, elongated body defining a proximal end and a distal end into an esophagus of the living being and locating the distal end of the elongated body proximate the cardiac tissue. The method further includes the step of directing a set of electromagnetic radiation from the distal end of the elongated body towards the cardiac tissue. The radiation activates the photodynamic substance leading to tissue necrosis.

A system for ablation of cardiac tissue in accordance with one embodiment of the present teachings may include a deformable, elongated body defining a proximal end and a distal end, the elongated body configured to be received within an esophagus of the living being. The system may further include a deformable membrane coupled to the elongated body proximate the distal end, the membrane covering a port in a wall of the elongated body and defining an expandable space between an interior surface of the membrane and an exterior surface of the elongated body. The system may further include an electromagnetic radiation source and an electronic control unit configured to selectively activate the electromagnetic radiation source to direct a set of electromagnetic radiation from the distal end of the elongated body to the cardiac tissue, the tissue containing a photodynamic substance.

A system for ablation of cardiac tissue in accordance with another embodiment of the present teachings may include a deformable, elongated body defining a proximal end and a distal end, the elongated body configured to be received within an esophagus of the living being. The system may further include an electromagnetic radiation source and an electronic control unit configured to selectively activate the electromagnetic radiation source to direct a set of electromagnetic radiation from the distal end of the elongated body to the cardiac tissue, the tissue containing a photodynamic substance. The distal end of the elongated body includes a reflective surface configured to direct the set of electromagnetic radiation.

The above-described system and method are advantageous because they provide a less invasive form of cardiac ablation as compared to current treatment methodologies and systems. In particular, the use of photodynamic therapy allows ablation of cardiac tissue via the esophagus thereby eliminating the need for surgical incisions and for maneuvering the ablation catheter through the circulatory system. As a result, the risk of complications for the patient is minimized and recovery time is reduced. The use of the deformable membrane also is advantageous because it provides a means for precise positioning of the distal end of the elongated body within the esophagus. In this manner, a stable reference point for evaluation and delivery of treatment can be established. Further, the distance of travel for the electromagnetic radiation and the obstacles through which the radiation would normally have to travel are reduced. The use of a reflective surface to direct the electromagnetic radiation is also advantageous because a greater percentage of radiation generated by the radiation source is directed to the tissue to be treated, increasing therapeutic efficiency.

The foregoing and other aspects, features, details, utilities and advantages of the present invention will be apparent from reading the following description and claims, and from reviewing the accompanying drawings.

BRIEF DESCRIPTION OF THE DRAWINGS

FIG. 3 is a diagrammatic view of a second system in accordance with the present teachings.

FIG. 4 is an enlarged diagrammatic view of one portion of the system of FIG. 3.

DETAILED DESCRIPTION OF EMBODIMENTS OF THE INVENTION

Figure 1:
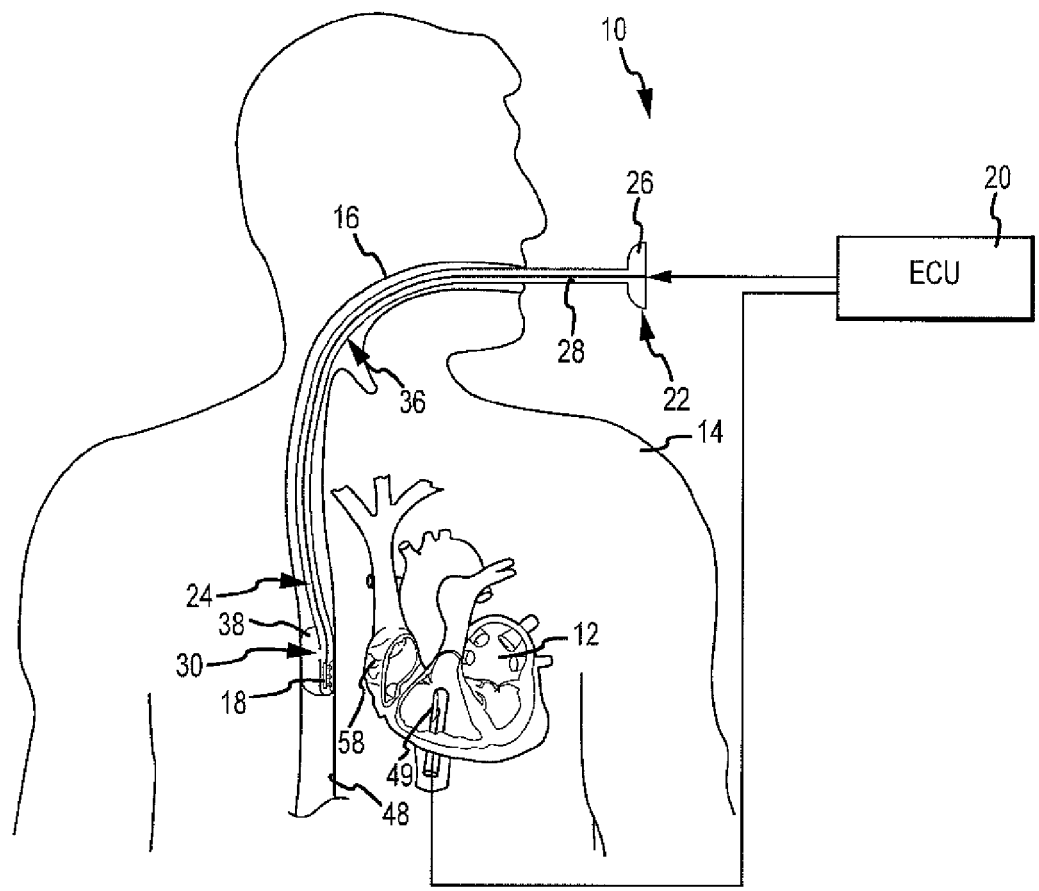
FIG. 1 is diagrammatic view of a first system in accordance with the present teachings.

Referring now to the drawings wherein like reference numerals are used to identify identical components in the various views, FIG. 1 illustrates one embodiment of a system 10 for ablation of cardiac tissue 12 in a patient's body 14. In one embodiment, the tissue 12 comprises the atrial epicardium. It should be understood, however, that the system 10 may find application in connection with ablation of various cardiac tissues. The system 10 may include a deformable, elongated body 16, an electromagnetic radiation source 18, and an electronic control unit (ECU) 20.

The elongated body 16 functions as a catheter and is provided to house the radiation source 18 and associated electronics, including electrical signal conductors and possibly processing circuits (e.g., filtering, amplification, and other signal conditioning circuitry). The elongated body 16 may also allow removal of bodily fluids or delivery of fluids and medicine into the patient's body 14. The elongated body 16 may further provide a means for transporting surgical tools or other instruments within the patient's body 14. The elongated body 16 may be formed from conventional materials such as polyurethane. The elongated body 16 is deformable and may be tubular and may be guided within the body 14 by a guide wire or other means known in the art. The elongated body 16 has a proximal end 22 and a distal end 24 (as used herein, "proximal" refers to a direction toward the body of a patient and away from the clinician, and "distal" refers to a direction toward the clinician and away from the body of a patient). The proximal end 22 may terminate in an electrical connector 26 for connection to the ECU 20. The elongated body 16 defines a lumen 28 extending between the proximal end 22 and the distal end 24. A port 30 and an opening 32 (shown in FIG. 2A) may be formed on substantially diametrically opposite points on a lateral wall 34 of the elongated body 16 for reasons described hereinbelow. In accordance with the present teachings, the elongated body 16 is inserted into the patient's body 14 via the esophagus 36 and maneuvered within the esophagus 36 to a position near a region of interest in the tissue 12.

Figures 2A, 2B:
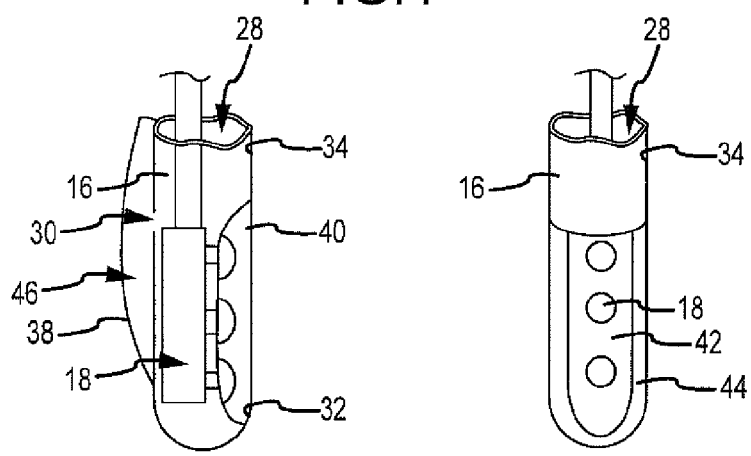
FIGS. 2A and 2B are enlarged plan views of one portion of the system of FIG. 1.

Referring to FIGS. 2A and 2B, in accordance with certain aspects of the present teachings, the distal end 24 of the elongated body 16 may include one or more structural features configured to position the distal end 24 within the esophagus 36 and to direct electromagnetic radiation from the radiation source 18. These features may include, for example, a deformable membrane 38, a lens 40, and reflective and opaque surfaces 42, 44.

The membrane 38 provides a means for positioning the distal end 24 of the elongated body 16 within the esophagus 36. The membrane 38 may be made from conventional materials including urethane such as manufactured by Advanced Polymers Inc., 13 Industrial Way, Salem, N.H. 03079 USA. The membrane 38 is coupled to the elongated body 16 proximate the distal end 24 and covers the port 30 in the wall 34 of the elongated body 16. The membrane 38 is mounted to the elongated body 16 by using an adhesive such as UV adhesive. The membrane 38 defines an expandable space 46 between an interior surface of the membrane 38 and an exterior surface of the wall 34 of the elongated body 16. Fluid may be provided through the lumen 28 and/or the port 30 in the elongated body 16 and into the space 46 to deform the membrane 38 and expand the space 46. The fluid may comprise, for example, air (pneumatic fluid), water, or a radiopaque solution. The membrane 38 may be substantially diametrically opposite the opening 32. Upon deformation or inflation of the membrane 38, the distal end 24 of the elongated body 16 is urged to a position in which the distal end 24—and particularly the opening 32—are disposed against a wall 48 (see FIG. 1) of the esophagus 36.

The use of the membrane 38 provides several advantages. First, the membrane 38 places the distal end 24 of the elongated body 16 in a stable position and, therefore, provides a stable reference point that can be used by the ECU 20 in the evaluation and delivery of therapeutic ablation. Second, by placing the distal end 24 against the wall 48, the delivery of electromagnetic radiation is enhanced by reducing the distance of travel for the radiation and permitting stable directional focus of the electromagnetic energy toward the intended target. Although only one membrane 38 is shown in the illustrated embodiment, multiple membranes could be used. In particular, additional membranes could be mounted to the elongated body 16 and expanded or inflated using fluid through corresponding ports in the elongated body 16 to allow for more precise positioning and stability.

The lens 40 is provided to allow transmission of radiation from the radiation source 18 while protecting the source 18 and the other electronic components from potential damage due to, for example, contact with bodily fluids. The lens 40 may be made from glass, such as crown glass; or conventional plastics, such as polycarbonate, polymethyl methacrylate (PMMA or acrylic), and allyl diglycol carbonate (sold under the registered trademark "CR-39" by PPG Industries, Pittsburgh, Pa. 15272 USA); or a gel, such as hydrogel or silicone hydrogel; or photoresist materials such as SU-8. The lens 40 covers the opening 32 in the wall 34 of the elongated body 16. The lens 40 extends about only a portion of the circumference of the elongated body 16 and may have an elliptical curve to focus the electromagnetic radiation.

The surfaces 42, 44 are provided to control emission of electromagnetic radiation from the distal end 24 of the elongated body 16. The surface 42 reflects radiation emitted by the source 18 in a direction opposite the wall 48 of the esophagus 36 back towards the wall 48 to increase therapeutic efficiency. The surface 42 is reflective and may comprise a mirror which may be attached to the radially inner side of the lens 40 using an adhesive. The lens 40 and the surface 42 may be deformable such that the curvature and focal length of the lens 40 and/or of the surface 42 can be manipulated by flexing the elongated body 16 and/or adjusting the fluid pressure in the space 46 within the membrane 38 (in a manner analogous to the lens in the human eye, which alters its shape, and consequently its focal length, in response to changes in zonular tension induced by ciliary muscle contraction). The surface 44 is opaque and inhibits passage of electromagnetic radiation emitted by the source 18 in directions away from the wall 48 of the esophagus 36. The surface 44 may extend about a portion of the circumference of the elongated body 16 on either side of the lens 40. The surface 44 may comprise an absorptive coating on the radially inner surface of the wall 34. The surface 44 may extend around about half (180°) of the circumferential surface of the wall and may be centered behind the reflective surface 42.

Referring again to FIG. 1, the electromagnetic radiation source 18 is provided to generate a set of electromagnetic radiation for delivery to the tissue 12. The source 18 may comprise, for example, a light emitting diode (LED) or laser (e.g., a laser diode). The source 18 may produce a monochromatic or spectral radiation, and the radiation may be polarized or unpolarized. The source 18 may generate radiation at various points along the electromagnetic spectrum including, for example, visible light, infrared, near infrared, ultraviolet, and near ultraviolet radiation. The radiation source 18 may emit radiation in a controlled manner responsive to signals received from the control unit 20.

The system 10 may also include an electromagnetic radiation sensor 49. The sensor 49 is provided to generated a signal in response to electromagnetic radiation originating from the tissue 12 in response to radiation transmitted by the source 18. This signal may be used by the ECU 20 to measure the radiation incident on the tissue 12 in order to assist in positioning the source 18, to titrate radiation levels to effect therapy, and to assess tissue necrosis (lesion creation). The radiation originating from the tissue 12 may comprise a portion of the radiation emitted from the source 18 or may comprise radiation reflected or emitted by a photodynamic substance in the tissue 12 as described in greater detail below. The sensor 49 may comprise a photodiode. As shown in FIG. 1, the sensor 49 may be supported at the distal end of another elongated, deformable body (e.g., a catheter) and, in accordance with one aspect of the present teachings, may be positioned on the opposite side of the tissue 12 that is being treated relative to the distal end 24 of elongated body 16. For example, the sensor 49 may be positioned within a heart chamber on the endocardial side of the tissue 12 and may receive radiation originating from the tissue 12 in response to radiation emitted from the source 18 on the epicardial side of the tissue 12. Alternatively, the sensor 49 may be located within the elongated body 16 at the distal end 24 of the elongated body 16 proximate the source 18.

The electronic control unit ("ECU") 20 provides a means for selectively activating the source 18 to direct a set of electromagnetic radiation to the tissue 12. The ECU 20 may comprise a programmable microprocessor or microcontroller or may comprise an application specific integrated circuit (ASIC). The ECU 20 may include a central processing unit (CPU) and an input/output (I/O) interface through which the ECU 20 may receive a plurality of input signals including signals generated by various feedback sensors on or remote from the elongated body 16 and generate a plurality of output signals to convey information regarding the operation of the radiation source 18 and the effects of treatment. These output signals may convey information through variation in amplitude of frequency of voltage or current and may, for example, be used to generate images relating to the tissue 12 on a conventional display monitor (not shown). The input and output signals may comprise electrical signals. Alternatively, signals may be transmitted wirelessly in a conventional manner.

In the embodiment shown in FIGS. 1, 2A and B, the radiation source 18 is disposed at the distal end 24 of the elongated body 16 and the radiation sensor 49 is likewise disposed at the distal end of another body. Referring now to FIG. 3, in another embodiment of the system 10' a radiation source 18' is disposed proximate the proximal end 22 of the elongated body 16 while a radiation sensor 49' may likewise be disposed proximate the proximal end of another body. Radiation from the radiation source 18' is transmitted to the distal end 24 through one or more optic fibers 50. Similarly, radiation may be collected at the distal end of the other body and provided to the sensor 49' through one or more fibers 50. The fibers 50 are conventional and may be made from various glass compositions (e.g., silica) or plastics (e.g., polymethyl methacrylate (PMMA) surrounded by fluorinated polymers). The fibers 50 include a core and a cladding with the core having a higher refractive index than the cladding. The fibers 50 may further include a buffer layer and a jacket as is known in the art. The fibers 50 may, for example, comprise any of a variety of common fibers sold by Polymicro Technologies, Inc., Edmund Optics, Inc., or Keyence Corporation. The fibers 50 are disposed within the elongated body 16 and may extend from the proximal end 22 to the distal end 24 of the elongated body 16 where they terminate at the lens 40. Again, although the sensor 49' is illustrated as disposed at the end of a separate elongated body, the sensor 49' could alternatively be located at the proximal end 22 of the elongated body 16, and radiation could be received through the same fiber in the elongated body 16 through which radiation is transmitted or another fiber within the elongated body 16.

The radiation transmitted by the fiber 50 may be controlled or amplified using different components. Referring to FIG. 4, a filter 52 may be disposed within the fiber 50 or may cover the proximal or distal end of the fiber 50 to control the passage of radiation by permitting passage of radiation of a selected wavelength (or range of wavelengths) while filtering out optical noise. A lens 54 may also be used to focus the radiation exiting the fiber 50. The lens 54 may be located at the distal end of the fiber 50. Alternatively, the lens 40 may be shaped to focus the transmission of radiation.

Figure 5:
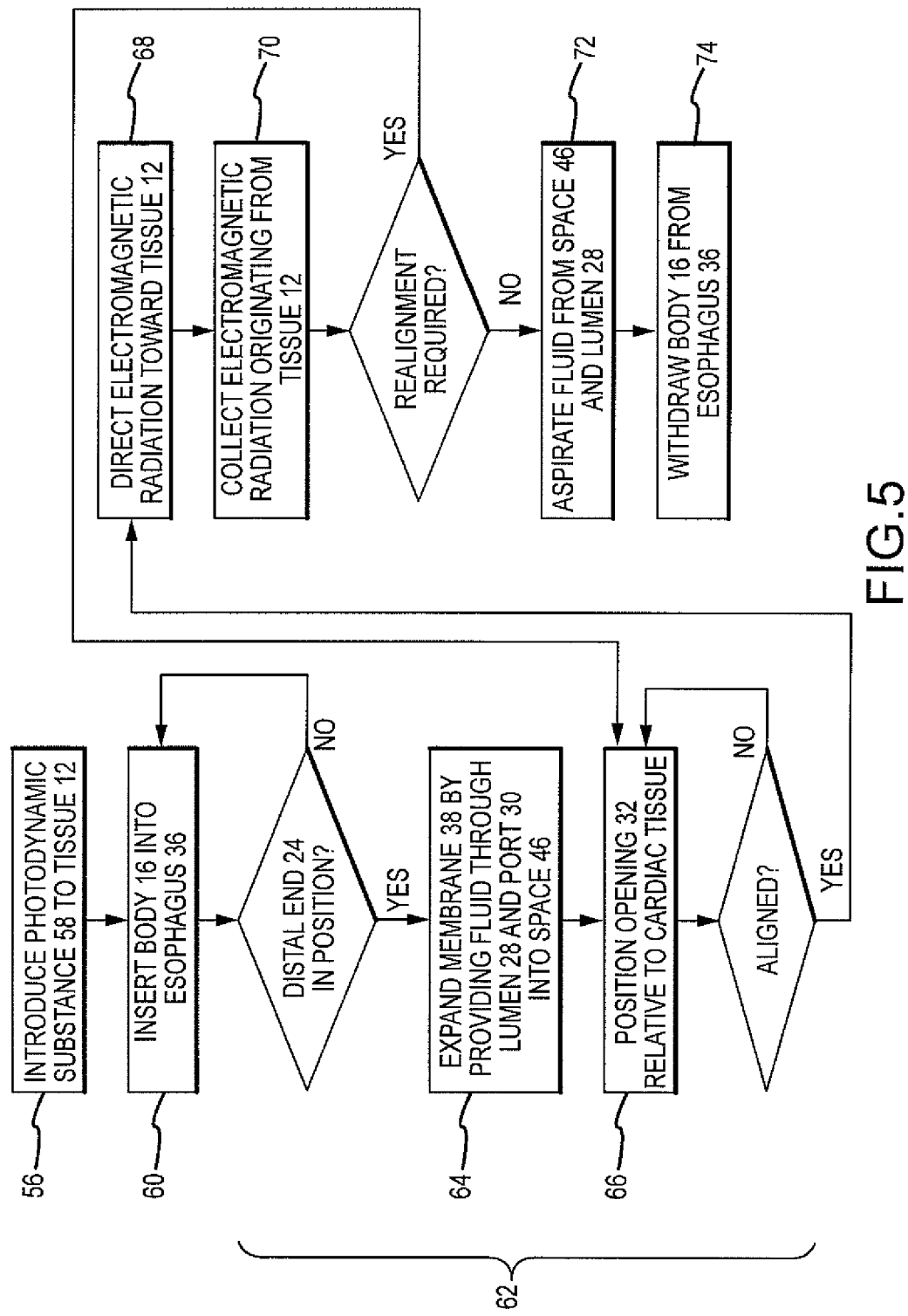
FIG. 5 is a flow chart diagram illustrating a method in accordance with the present teachings.

Referring now to FIG. 5, a method for ablation of cardiac tissue 12 in accordance with the present teachings will be described. The method may begin with the step 56 of introducing a photodynamic substance 58 (see FIG. 1) to the tissue 12. The substance 58 is relatively inert until activated by radiation of a specific wavelength. Upon activation, the substance 58 induce tissue necrosis through a variety of methods such as apoptosis. The substance 58 may comprise a photosensitive chemical or drug or other substance. For example, the substance 58 may comprise 5-aminolevulinic acid (ALA), meso-tetra-hydroxyphenyl-chlorin (mTHPC); an electrochromic and potentiometric dye such as di-2-ANEPEQ, di-4-ANEPPS, or di-8-ANEPPS; neuromodulators such as Acetylcholine; a cardioplegic solution; or a cryocardioplegic solution (e.g., hypothermic saline). The substance 58 may comprise the substance (porfimer sodium) sold by Axcan Pharma Inc. under the registered trademark "PHOTOFRIN" or the substance sold by Scotia Holdings plc under the registered trademark "FOSCAN." Alternatively, the substance 58 may be a radiopaque substance such as the substance sold by Amersham Health AS under the registered trademark "HYPAQUE" or any of a variety of conventional radiopaque dyes. The substance 58 may also comprise a substance that modifies electrical conductivity in the tissue 12 such as saline, one of the above-identified photosensitizes, or an antistenotic agent. The substance 58 may also comprise a cytotoxic chemical.

The substance 58 may be introduced into the tissue 12 in a variety of ways such that the substance 58 is absorbed into the cells in the tissue 12 or binds with the cell membranes. For example, the substance 58 may be introduced through in-situ delivery, arterial delivery and/or systemic delivery. One method of in-situ delivery may be through electroporation in which a site limited electric shock is used to create an electric field to cause expansion of the cells in the tissue 12 for a period of time to allow the substance 58 to enter the cells. Alternative methods of in-situ delivery may be by application of an electrical field on the substance 58 itself or using acoustic waves (e.g. ultrasound) to break through the tissue boundary. Alternatively, the substance 58 may be infused through the artery, such as the coronary artery, to allow perfusion into the tissue 12. It should be understood that these methods of introducing the substance 58 to the tissue 12 are exemplary only and not intended to limit the scope of the invention.

It should be understood that the system and method according to the present teachings may also involve use of multiple photodynamic substances 58. For example, diagnosis or treatment may occur in a region of interest having multiple tissue types. Because different tissues react differently to the substances 58 (e.g., some tissues are more responsive than others), it may be advantageous to use different substances within the same region of interest.

The method according to the present teachings may further include the step 60 of inserting the elongated body 16 into the esophagus 36. The elongated body 16 may be inserted by the physician in a conventional manner through the mouth or nose and into the esophagus 36.

The method may further include the step 62 of locating the distal end 24 of the elongated body 16 proximate the tissue 12. The physician may maneuver the elongated body 16 using a guide wire or in other conventional manners through the esophagus 36 to a position at which treatment can be provided to the tissue 12. In accordance with one aspect of the present teachings, step 62 may include the substep 64 of expanding the space 46 between the exterior surface of the elongated body 16 and the interior surface of the membrane 38. As discussed hereinabove, this step may include the substep of providing fluid to the space 46 through the lumen 28 and the port 30 in the wall 34 of the elongated body 16. The expansion of the membrane 38 and the space 46 urges the distal end 24 into engagement with the esophageal wall 48 for positional stability and a reduction in scattering and transmission distance for the electromagnetic radiation generated by the radiation source 18. After expansion of the membrane 38 and the space 46, step 62 may further include the substep 66 of positioning the opening 32 relative to the tissue 12.

The method may continue with the step 68 of directing electromagnetic radiation from the distal end 24 of the elongated body 16 towards the tissue 12. As discussed above, the electromagnetic radiation activates the substance 58 in the tissue 12 leading to tissue necrosis. Also as discussed above, the radiation may be generated from a source 18 located at the distal end 24 of the elongated body 16 or from a source 18' located remote from the distal end 24 of the elongated body 16. The method may further include the step 70 of collecting electromagnetic radiation originating from the tissue 12 in response to the radiation emitted from the distal end 24 of the elongated body 16. As discussed above, radiation may be collected on an opposite side of the tissue 12 relative to the distal end 24 of the elongated body 16 (e.g., within a heart chamber on the endocardial side of the tissue 12) and provided directly to the sensor 49 located at the distal end of another elongated body or indirectly to the sensor 49' located at the proximal end of the elongated body via one or more fibers 50. Radiation may alternatively be collected at the distal end 24 of the elongated body 16 by sensors 49, 49' located at the distal or proximal ends 24, 22 of the elongated body 16. The distal end 24 of the elongated body 16 and the opening 32 may be realigned and step 68 may be repeated to the extent necessary for proper treatment.

Once ablation of the tissue 12 is complete, the method may continue with the step 72 of aspirating fluid from the space 46 and the lumen 28 to deflate the membrane 38. The method may conclude the step 74 of withdrawing the elongated body 16 from the esophagus 36.

A system and method in accordance with the present teachings offers one or more of a number of advantages. For example, the system and method provide a less invasive form of cardiac ablation as compared to various current treatment methodologies and systems. The use of photodynamic therapy allows ablation of cardiac tissue via the esophagus thereby eliminating the need for surgical incisions or for maneuvering an ablation catheter through the circulatory system. As a result, both the risk of complications for the patient and the recovery time are reduced.

Although several embodiments of this invention have been described above with a certain degree of particularity, those skilled in the art could make numerous alterations to the disclose embodiments without departing from the scope of this invention. For example, although the illustrated embodiments shows a single radiation source 18 or 18' and a single optic fiber 50 used in connection with source 18', multiple radiation sources could be employed to enable radiation to be transmitted using different radiation characteristics (e.g., frequency, intensity, phase angle, polarization) for use in generating a variety of therapeutic effects. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for ablation of cardiac tissue in a living being, the system comprising the following:
    a deformable, elongated body defining a proximal end and a distal end, said elongated body configured to be received within an esophagus of said living being;
    a first electromagnetic radiation source;
    an electronic control unit configured to selectively activate said first electromagnetic radiation source to direct a first set of electromagnetic radiation from said distal end of said elongated body to said cardiac tissue, said tissue containing a photodynamic substance;
    an electromagnetic radiation sensor external to and remote from said elongated body and configured to collect a second set of electromagnetic radiation originating from said cardiac tissue in response to said first set of electromagnetic radiation; and
    an optic fiber configured to be disposed on a side of said cardiac tissue opposite said distal end of said elongated body, wherein the optic fiber is in communication with said electromagnetic radiation sensor.

2. The system of claim 1, further comprising:
    a deformable membrane coupled to said elongated body proximate said distal end, said membrane covering a port in a wall of said elongated body and defining an expandable space between an interior surface of said membrane and an exterior surface of said elongated body;
    wherein said distal end of said elongated body includes an opening in a lateral wall of said elongated body, said first set of electromagnetic radiation exiting through said opening and said membrane is diametrically opposite said opening.

3. The system of claim 2, wherein said electromagnetic radiation source is located at said distal end of said elongated body.

4. The system of claim 2, further comprising an optic fiber disposed within said elongated body, said electromagnetic radiation source located proximate said proximal end of said elongated body and configured to direct said first set of electromagnetic radiation through said optic fiber.

5. The system of claim 1 wherein said distal end of said elongated body includes a reflective surface configured to direct said first set of electromagnetic radiation.

6. The system of claim 5, wherein said reflective surface comprises a mirror.

7. The system of claim 1, wherein said distal end of said elongated body further includes an opaque surface that inhibits passage of said first set of electromagnetic radiation in a first direction.

8. The system of claim 1 wherein said electromagnetic radiation source is located at said distal end of said body.

9. The system of claim 1, further comprising an optic fiber disposed within said body, said electromagnetic radiation source located proximate said proximal end of said body and configured to direct said first set of electromagnetic radiation through said optic fiber.

* * * * *